US00PP33136P2

(12) United States Plant Patent
Olesen

(10) Patent No.: US PP33,136 P2
(45) Date of Patent: Jun. 8, 2021

(54) MINIATURE ROSE PLANT NAMED 'POULPAH102'

(50) Latin Name: *Rosa hybrida*
Varietal Denomination: Poulpah102

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,986

(22) Filed: Sep. 3, 2020

(51) Int. Cl.
*A01H 5/02* (2018.01)
*A01H 6/74* (2018.01)

(52) U.S. Cl.
USPC ..... Plt./121

(58) Field of Classification Search
USPC ..... Plt./101, 116, 121
See application file for complete search history.

(56) References Cited

PUBLICATIONS

Poulsen Roser website. (https://www.poulsenroser.dk/da/roses/ShowProduct/68755). Retrieved from the internet Nov. 20, 2020. 2 pages. (Year: 2020).*

* cited by examiner

*Primary Examiner* — Susan McCormick Ewoldt
*Assistant Examiner* — Karen M Redden

(57) ABSTRACT

A new garden rose plant of the miniature class which has abundant, deep pink flowers, strong perfume, and attractive foliage. This new and distinct variety has shown to be uniform and stable in the resulting generations from asexual propagation.

3 Drawing Sheets

Botanical designation: *Rosa hybrida.*
Variety denomination: 'Poulpah102'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulpah102', originated as a single seedling from the stated cross.

The new variety may be distinguished from its male pollen parent and female seed parent primarily by the following characteristics. The male pollen parent plant has red flowers and grows to a height of 100 cm while the new variety has deep pink flowers and grows to a height of 40 cm. The female seed parent plant has pink and white striped flowers while the new variety has deep pink flowers without stripes.

The objective of the hybridization of this rose variety was to create a new and distinct variety with unique qualities, such as:

1. Uniform and abundant deep pink flowers with strong perfume;
2. Vigorous, but compact growth when propagated on its own roots;
3. Exceptional disease resistance.

This combination of qualities is not present in previously available commercial cultivars of this type, known to the inventor, and distinguish 'Poulpah102' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulpah102' was selected in the spring of 2014 by the inventor as a single plant from the progeny of the aforementioned hybridization.

Asexual reproduction of 'Poulpah102' by rooted cuttings was first done by Mogens N. Olesen in the nursery in Fredensborg, Denmark in July, 2014. This initial and other subsequent asexual propagations conducted in controlled environments have demonstrated that the characteristics of 'Poulpah102' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah102'.

Specifically illustrated in FIG. 1 of the drawings are flower petals and sepals detached, showing reproductive flower parts and general quantity of petals.

Figure 1:
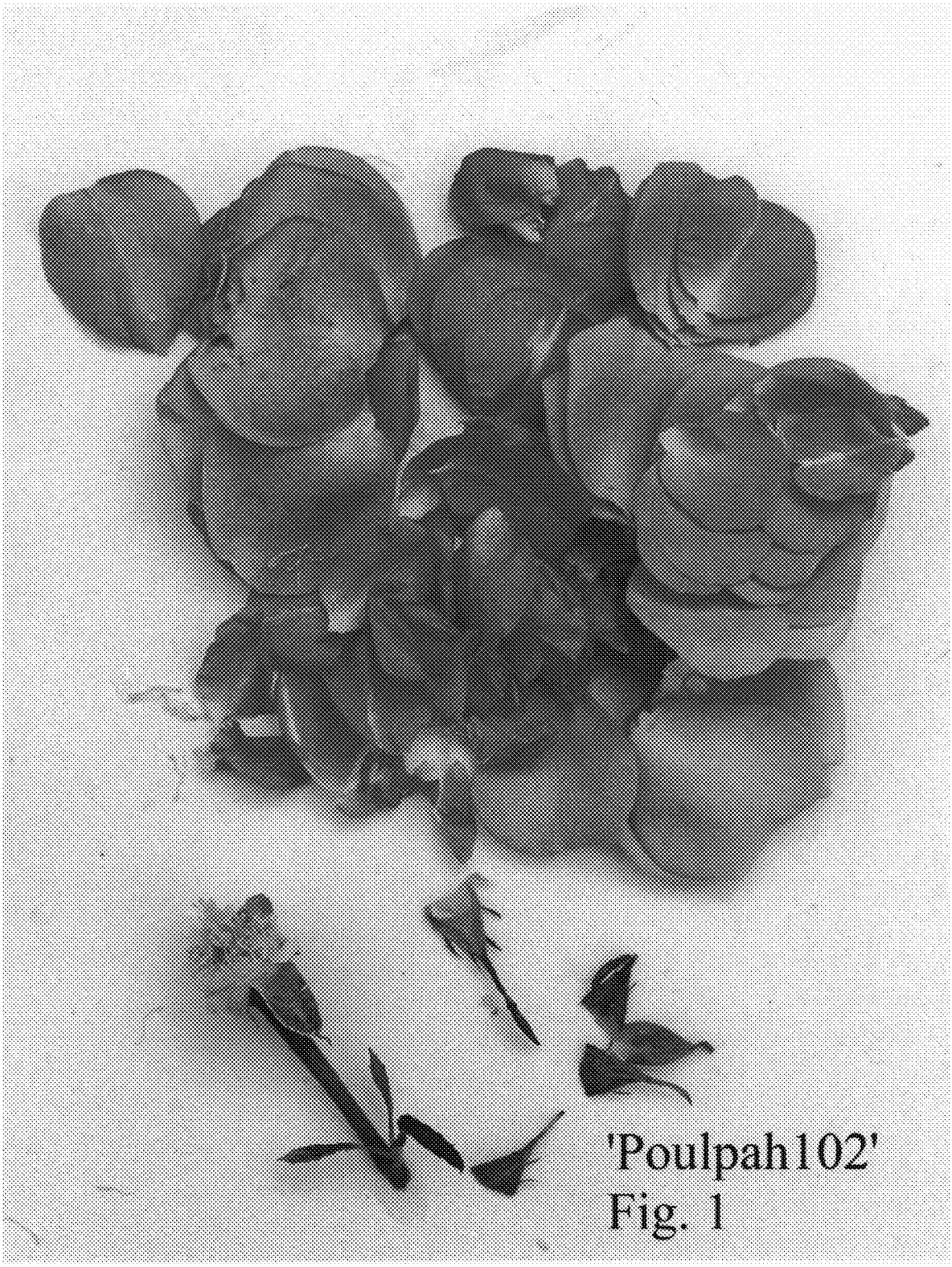
Figure 2:
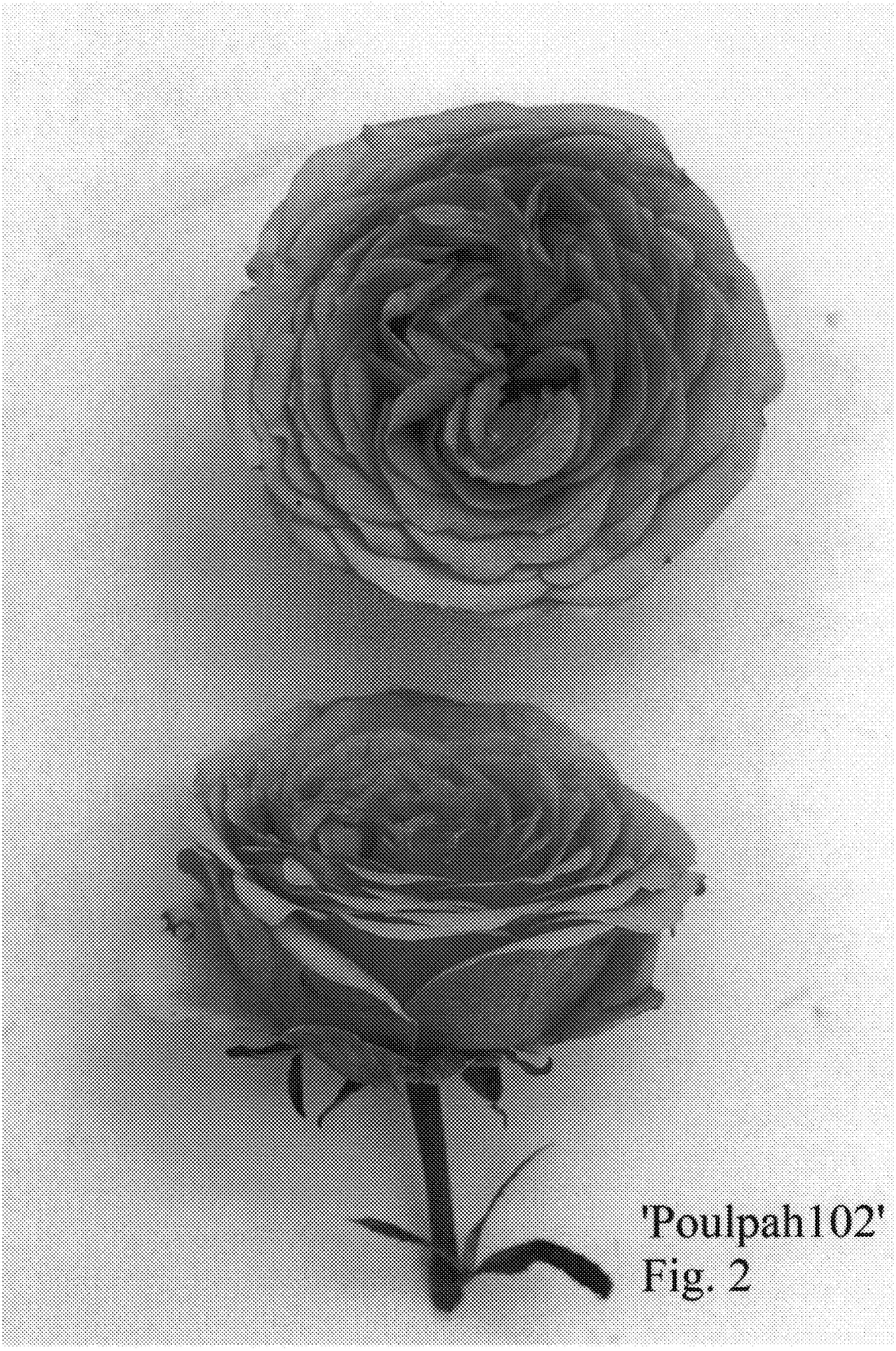

Specifically illustrated in FIG. 2 of the drawings are open flowers viewed from above and from the side.

Figure 3:
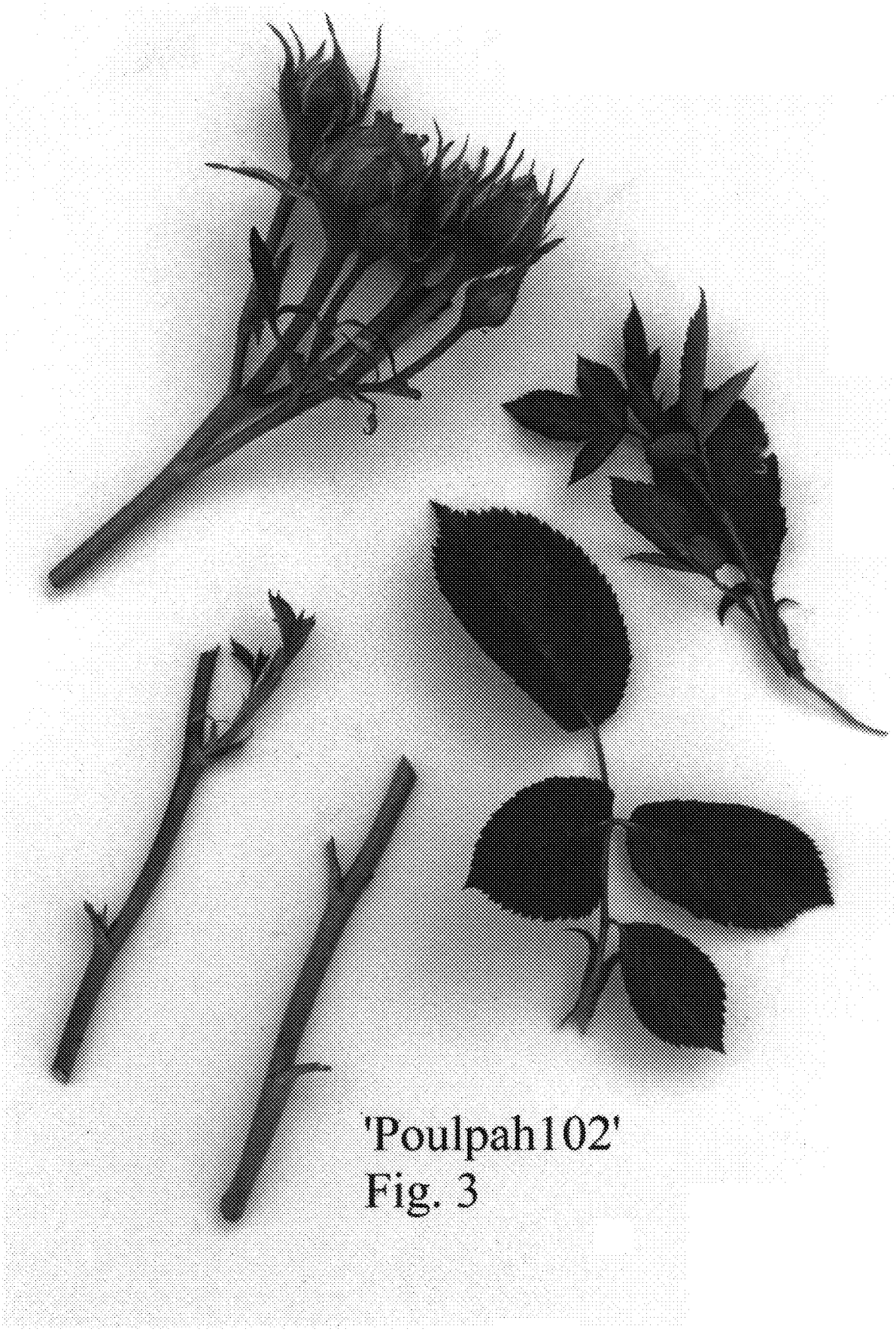

Specifically illustrated in FIG. 3 of the drawings is a cluster of flower buds on the branch, a mature leaf, juvenile leaves and bare stems. Plants shown are 2 years of age.

DETAILED DESCRIPTION OF THE VARIETY

The following is a description of 'Poulpah102', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah082', U.S. Plant Pat. No. 29,650 are compared to 'Poulpah102' in Chart 1.

CHART 1

| | 'Poulpah102' | 'Poulpah082' |
|---|---|---|
| Petal Count | 85 to 90 | 35 |
| Flower Diameter | 80 mm | 90 mm |
| General Tonality of Flower Color | Red-Purple Group N57C | Red-Purple Group 58C & 62B |

FLOWER AND FLOWER BUD

Blooming habit: Continuous.

Flower bud:

*Size.*—Upon opening, 25 mm in length from base of receptacle to end of bud. Bud diameter is 20 mm.

*Bud form.*—Ovoid.

*Bud color.*—As sepals divide petals are Green- White Group 157A with intonations of Greyed-Red Group 182C and Red-Purple Group 63B.

*Sepal inner surface.*—Color: Yellow-Green Group 146D with intonations of Greyed-Orange Group 175B. Surface: Lightly pubescent.

*Sepal outer surface.*—Color: Yellow-Green Group 144A with intonations of Greyed-Red Group 179A. Texture: Smooth.

*Sepal shape.*—Apex: Cirrhose. Base: Flat at union with receptacle.

*Sepal margin.*—Margins have weak to moderate foliaceous appendages on three of the five sepals.

*Sepal size.*—20 mm long, 10 mm wide.

*Receptacle.*—Texture: Smooth. Size: 7 mm in height, 10 mm wide. Color: Yellow-Green Group 144A. Shape: Funnel.

*Pedicel.*—Surface: Smooth. Length: 25 to 35 mm. Diameter: 3 mm on average. Color: Yellow-Green Group 144B with intonations of Greyed-Red Group 178C. Strength: Strong.

*Peduncle.*—Length: 1 to 3 cm. Diameter: 3 or 4 mm. Color: Yellow-Green Group 144B with intonations of Greyed-Red Group 178C. Texture: Smooth.

Flower bud development: Flower buds are borne in clusters of about 5 to 7 flower buds per stem.

Flower bloom:

*Fragrance.*—Strong rose perfume.

*Duration.*—The blooms have a duration on the plant of approximately 18 days. Petals fall cleanly away from plant after flowers have fully matured.

*Size.*—Flower diameter is 80 mm when open. Flower depth is 30 mm.

*Flower shape.*—Quartered-rosette, very double, with many overlapping petals packed into quarter sections.

*Shape of flower, side view.*—The upper portion is flat, and the lower portion is concave.

Petalage: Under normal conditions, flowers have about 85 to 90 petals.

General tonality of flower: Open flowers are Red-Purple Group N57C.

Petal color:

*Upon opening, outer petals.*—Upper surface: Red-Purple Group 62A. Lower surface: Red-Purple Group 67C splashed with Red-Purple Group 69B.

*Upon opening, inner petals.*—Upper surface: Red-Purple Group 58B splashed with Red-Purple Group 62C. Lower surface: Red-Purple Group 63B splashed with Red-Purple Group 65C.

*Basal petal spots, upon opening.*—Upper surface: Green-White Group 157B. Lower surface: Green-White Group 157B.

*After opening, outer petals.*—Upper surface: Red-Purple Group 62A. Lower surface: Red-Purple Group 67C splashed with Red-Purple Group 69B.

*After opening, inner petals.*—Upper surface: Red-Purple Group 58B splashed with Red-Purple Group 62C. Lower surface: Red-Purple Group 63B splashed with Red-Purple Group 65C.

*Basal petal spots, after opening.*—Upper surface: Green-White Group 157A. Lower surface: Green-White Group 157A.

Petals:

*Petal reflex.*—Outer petals are slightly reflexed.

*Margin.*—Entire and uniform. No undulation.

*Shape.*—Broad and round. Apex shape: Rounded. Base shape: Rounded.

*Size.*—45 mm (l)×40 mm (w).

*Texture.*—Smooth.

*Thickness.*—Average.

Petaloids:

*Size.*—15 mm (l) by 10 mm (w).

*Quantity.*—About 15.

*Shape.*—Elliptical with an acute base and rounded apices.

*Color.*—Upper surface is Red-Purple Group 58B splashed with Red-Purple Group 62C. The lower surface is Red-Purple Group 63B splashed with Red-Purple Group 65C. At the point of attachment on upper and lower surface there is a petaloid spot of Green-White Group 157A and Yellow Group 8D.

Reproductive flower parts:

*Pollen.*—None observed.

*Anthers.*—Size: 2 mm in length. Color: Yellow Group 3D. Quantity: 40 on average.

*Filaments.*—Color: Yellow Group 8A. Length: 6 mm.

*Pistils.*—Length: 10 mm. Quantity: 45 on average.

*Stigmas.*—Color: Green-White Group 157A.

*Styles.*—Color: Green White Group 157A.

*Location of stigmas.*—Superior in location relative to the length of the filaments and the height of the anthers.

*Hips.*—None Observed.

PLANT

Plant growth: Compact and upright. Plants are 34 cm in height, and 30 cm wide.

Stems:

*Color of juvenile growth.*—Yellow-Green Group 144B.

*Color of mature growth*.—Yellow-Green Group 144A.

*Length*.—Canes are about 18 cm from the base of the plant to the flowering portion.

*Diameter*.—About 10 mm.

*Internodes*.—On mature canes about 40 mm between nodes.

*Surface texture*.—Young wood: Smooth. Older wood: Somewhat rough with very small prickles.

Long prickles: None observed.

Plant foliage:

*Compound leaf*.—130 mm (l)×95 (w).

*Quantity*.—2 leaves per 10 cm of stem on average.

*Leaf bearing angle to the stem*.—45 degrees.

*Color of juvenile foliage*.—Upper side: Yellow-Green Group 144A with intonations of Greyed-Red Group 178A. Lower side: Yellow-Green Group 144A with intonations of Greyed-Red Group 178A.

*Color of mature foliage*.—Upper side: Yellow-Green Group 146A. Lower side: Yellow-Green Group 146B.

Plant leaves and leaflets:

*Stipules*.—Size: 18 mm long, 6 mm wide. Quantity: 2 per compound leaf. Shape: Linear, slightly broad based with outward extending apices. Margins: Finely serrated. Color:

*Petiole*.—Length: 35 mm. Diameter: 2 mm. Upper surface color: Yellow-Green Group 144A. Lower surface color: Yellow-Green Group 144A.

*Rachis*.—Length: 40 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 65 mm long, 40 mm wide. Shape: Generally elliptical. Base: Rounded. Apex: Mucronate. Texture: Smooth. Thickness: Average. Arrangement: Odd pinnate. Venation: Reticulate. Glossiness: Highly glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpah102', substantially as illustrated and described herein, due to its abundant deep pink flowers, strong perfume, disease resistance, and extended period of bloom.

* * * * *

'Poulpah102'

'Poulpah102'

'Poulpah102'